US011116387B2

(12) United States Patent
Masaki (10) Patent No.: US 11,116,387 B2
(45) Date of Patent: Sep. 14, 2021

(54) INSERTION DEVICE AND ENDOSCOPE

(71) Applicant: Olympus Corporation, Hachioji (JP)

(72) Inventor: Yutaka Masaki, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 420 days.

(21) Appl. No.: 16/209,359

(22) Filed: Dec. 4, 2018

(65) Prior Publication Data

US 2019/0099059 A1    Apr. 4, 2019

Related U.S. Application Data

(63) Continuation of application No. PCT/JP2017/011166, filed on Mar. 21, 2017.

(30) Foreign Application Priority Data

Jun. 13, 2016    (JP) .............................. JP2016-117103

(51) Int. Cl.
*A61B 1/00*        (2006.01)
*A61B 1/06*        (2006.01)
(Continued)

(52) U.S. Cl.
CPC ........ *A61B 1/0016* (2013.01); *A61B 1/00073* (2013.01); *A61B 1/00087* (2013.01);
(Continued)

(58) Field of Classification Search
None
See application file for complete search history.

(56) References Cited

U.S. PATENT DOCUMENTS

2012/0029281 A1    2/2012  Frassica et al.
2012/0302831 A1    11/2012 Ashida et al.
(Continued)

FOREIGN PATENT DOCUMENTS

JP    2012-245052    12/2012
JP    2014-524807     9/2014
(Continued)

OTHER PUBLICATIONS

Apr. 30, 2020 Office Action issued in Chinese Patent Application No. 201780022281.2.
(Continued)

*Primary Examiner* — Timothy J Neal
(74) *Attorney, Agent, or Firm* — Oliff PLC (57) ABSTRACT

An insertion device includes an insertion portion in which a movable member is held in contact with an outer circumferential surface of a hollow cylindrical member. When drive power is transmitted from the hollow cylindrical member to the movable member as the hollow cylindrical member is rotated about a longitudinal axis of the insertion portion, the movable member is rotated around its own axis parallel to the longitudinal axis and moved around the (Continued)

longitudinal axis. The insertion portion includes a membrane covering the movable member from an outer circumferential side thereof. The membrane urges the movable member toward the longitudinal axis, thereby pressing the movable member against the outer circumferential surface of the hollow cylindrical member.

11 Claims, 3 Drawing Sheets

(51) Int. Cl.
  *A61B 1/005* (2006.01)
  *A61B 1/008* (2006.01)
  *A61B 1/01* (2006.01)
  *A61B 1/018* (2006.01)
  *A61B 1/07* (2006.01)
  *A61B 1/32* (2006.01)
(52) U.S. Cl.
  CPC ...... *A61B 1/00101* (2013.01); *A61B 1/00135* (2013.01); *A61B 1/00154* (2013.01); *A61B 1/00163* (2013.01); *A61B 1/0661* (2013.01); *A61B 1/008* (2013.01); *A61B 1/0055* (2013.01); *A61B 1/00133* (2013.01); *A61B 1/00156* (2013.01); *A61B 1/01* (2013.01); *A61B 1/018* (2013.01); *A61B 1/07* (2013.01); *A61B 1/32* (2013.01)

(56) References Cited

U.S. PATENT DOCUMENTS

| | | | |
|---|---|---|---|
| 2014/0330079 A1 | 11/2014 | Ishizaki et al. | |
| 2016/0249787 A1* | 9/2016 | Miyoshi | A61B 1/00073 |
| | | | 604/95.01 |

FOREIGN PATENT DOCUMENTS

| | | |
|---|---|---|
| JP | 2015-144782 | 8/2015 |
| WO | 2013038720 | 3/2013 |
| WO | 2013147017 | 10/2013 |
| WO | 2015072233 | 5/2015 |
| WO | 2015-118773 A1 | 8/2015 |

OTHER PUBLICATIONS

International Search Report and Written Opinion from corresponding International Application No. PCT/JP2017/011166, dated May 23, 2017.

* cited by examiner

INSERTION DEVICE AND ENDOSCOPE

CROSS-REFERENCE TO RELATED APPLICATIONS

This application is a continuation application of PCT Application No. PCT/JP2017/011166 filed on Mar. 21, 2017, which in turn claim priority to the Japanese Patent Application No. 2016-117103 filed on Jun. 13, 2016 in Japan which is hereby incorporated by reference in its entirety.

TECHNICAL FIELD

The technology disclosed herein relates to an insertion device having an insertion portion. The technology disclosed herein is also concerned with an endoscope having such an insertion device and a mount tool mounted in the insertion portion of the insertion device.

DESCRIPTION OF THE RELATED ART

PCT Patent Publication No. WO2013/038720 discloses an endoscope in which a helical unit is mounted on an insertion portion. The helical unit is a mount tool. In the endoscope, a drive shaft extends in the insertion portion, and has a distal end connected to a drive gear. A base portion and a rotor each of which is disposed on the insertion portion. An internal gear is formed on an inner circumferential surface of the rotor and is held in mesh with the drive gear. When the drive shaft rotates, a drive force is transmitted through the drive gear to the rotor that rotates around a longitudinal axis with respect to the base portion. The rotor has convexities, or inner convexities, projecting toward an outer circumferential side. The outer circumferential side of the rotor includes the convexities and is covered with a membrane on the insertion portion. The helical unit is detachably mounted on the insertion portion in covering relation to the outer circumferential side of the membrane. When the rotor rotates around the longitudinal axis, the convexities press the helical unit through the membrane. The drive force is thus transmitted to the helical unit, which rotates around the longitudinal axis.

In the aforementioned endoscope having the insertion device as disclosed in PCT Patent Publication No. WO2013/038720, the speed at which the convexities move around the longitudinal axis is not reduced with respect to the rotational speed of the internal gear, so that a rotational torque is not amplified between the internal gear and the convexities. Therefore, there is a possibility that the drive torque, or rotational torque, applied to the mount tool may be reduced. The drive torque applied to the mount tool can be increased by increasing the rotational torque applied to the internal gear. However, in order to increase the drive torque applied to the internal gear, it is necessary to increase the extent to which the drive torque is amplified in a structure that transmits the drive force from a drive source such as an electric motor or the like to the internal gear. If the extent to which the drive torque is amplified is increased in the structure that transmits the drive force from the drive source to the internal gear, then the structure that transmits the drive force in the insertion portion becomes complex. Therefore, an increased expenditure of labor and cost is required in the manufacture of the insertion portion.

BRIEF SUMMARY OF EMBODIMENTS

It is an object of the technology disclosed herein is to provide an insertion device in which a structure for transmitting a drive source in an insertion portion is simplified and a drive torque having an appropriate magnitude is applied to a mount tool. The insertion device is part of an endoscope system. In order to achieve the above object, in accordance with an aspect of the present disclosure, an insertion device includes an insertion portion extending along a longitudinal axis. The insertion portion includes a hollow cylindrical member along the longitudinal axis. The hollow cylindrical member is rotatable about the longitudinal axis by drive power transmitted to the hollow cylindrical member. At least one movable member is held in contact with an outer circumferential surface of the hollow cylindrical member. When the drive power is transmitted to the movable member from the hollow cylindrical member, the hollow cylindrical member is rotated around the longitudinal axis. The movable member is rotatable about its own axis parallel to the longitudinal axis and movable around the longitudinal axis. A membrane forms a part of an outer circumferential surface of the insertion portion in covering relation to the movable member from an outer circumferential side thereof. The membrane is flexible and urges the movable member toward the longitudinal axis. The membrane presses the movable member against the outer circumferential surface of the hollow cylindrical member.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Figure 1:
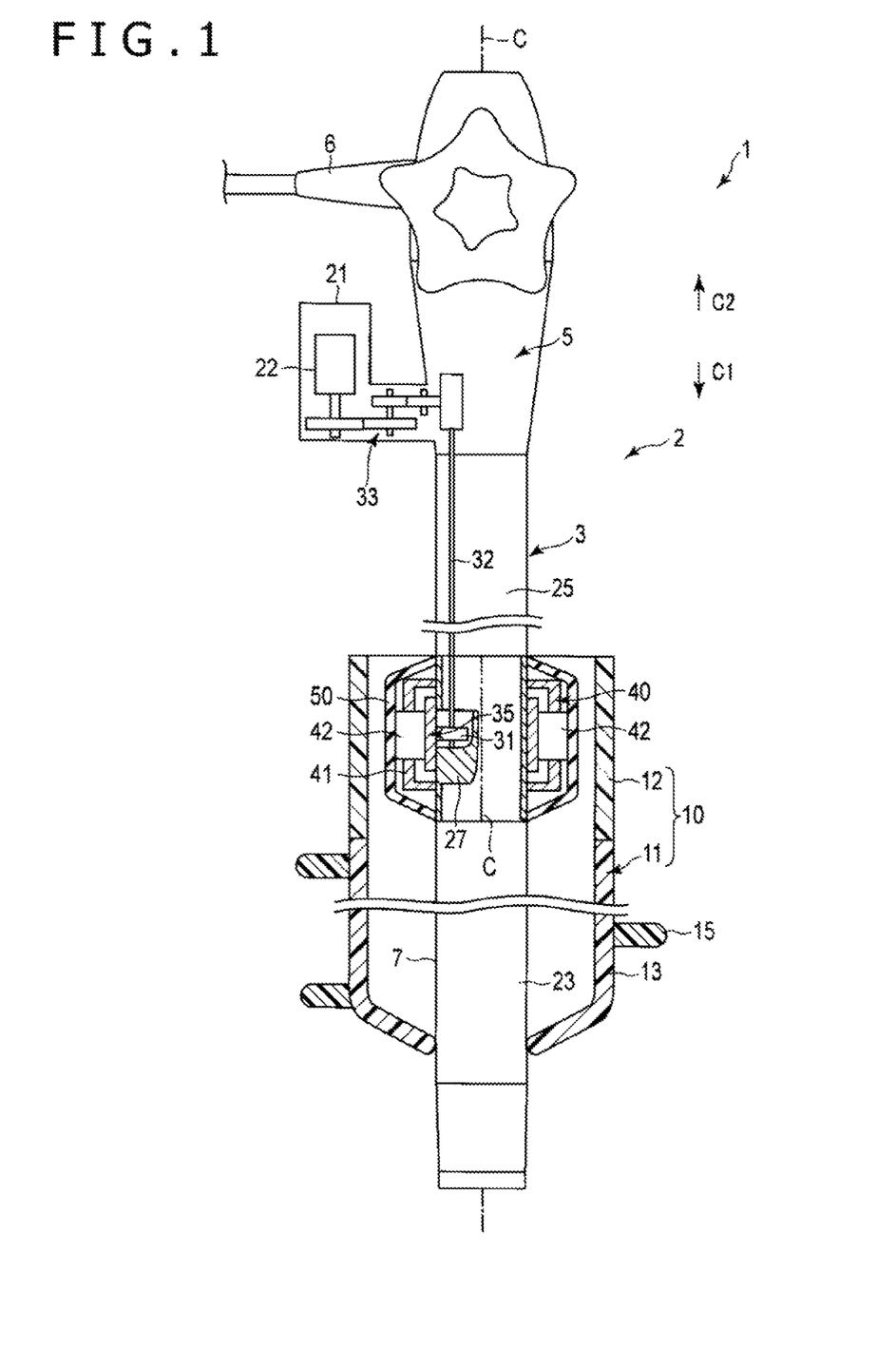
FIG. 1 is a schematic view of an endoscope which is part of an endoscope system not depicted for ease of illustration according to a first embodiment.

A first embodiment of the technology disclosed herein will be described hereinafter with reference to FIGS. 1 through 3. FIG. 1 is a view illustrating an endoscope 1. It should be noted that FIG. 1 illustrates an endoscope 1 that is a portion of an endoscope system that is not shown in FIG. 1 for ease of illustration. As illustrated in FIG. 1, the endoscope 1 includes an insertion device 2 and a helical unit 10 used as a mount tool. The insertion device 2 includes an insertion portion 3 having a longitudinal axis C used as a central axis thereof. One of directions, or longitudinal-axis directions, along the longitudinal axis C points to a distal end side C1. The other direction that is opposite the distal end side points to a proximal end side C2. The insertion portion 3 extends along the longitudinal axis C from the proximal end side toward the distal end side. The insertion portion 3 has an outer circumferential surface 7. The insertion device 2 includes a manipulator 5 on the proximal end side of the insertion portion 3. A universal cord 6 has an end connected to the manipulator 5.

The endoscope 1 is used with peripheral devices including an image processing device (not depicted) such as an image processor or the like, a light source device (not depicted) such as a lamp or the like, a drive control device (not depicted) including a power supply, a converter circuit, a processor, and a storage medium, an operation input device (not depicted) such as a foot switch or the like, and a display device (not depicted) such as a monitor or the like. The other end of the universal cord 6 is detachably connected to the light source device as one of the peripheral devices, for example.

In the insertion device 2, an image capturing cable (not depicted) and a light guide (not depicted) extend through the insertion portion 3, the manipulator 5, and the universal cord 6. An image capturing device (not depicted) such as a CCD or the like is disposed in a distal end portion of the insertion portion 3. The image capturing device captures an image of a subject through an observation window (not depicted) disposed on an outer surface of the distal end portion of the insertion portion 3. The image capturing device transmits a captured image signal through the image capturing cable to the image processing device (not depicted), which performs an image processing process. The image processing device thus generates an image of the subject, and the display device (not depicted) displays the generated image of the subject. Light emitted from the light source device (not depicted) is guided through the light guide. The light is applied through an illumination window (not depicted) disposed on the outer surface of the distal end portion of the insertion portion 3 to the subject.

The helical unit 10 is of a tubular shape. In the insertion device 2, the insertion portion 3 is inserted through the helical unit 10, or mount tool, that is detachably mounted on the outer circumferential surface 7 of the insertion portion 3. With the helical unit 10 mounted on the insertion portion 3, the central axis of the helical unit 10 is substantially coaxial with the longitudinal axis C of the insertion portion 3. The helical unit 10 has a driven portion 11 and a connector portion 12. The connector portion 12 is connected to the insertion portion 3. The driven portion 11 is coupled to a distal end side of the connector portion 12. The driven portion 11 includes a tubular tube body 13 and a helical fin 15. The tubular tube body 13 extends along the longitudinal axis C, or the central axis of the helical unit 10. The helical fin 15 projects outwardly from an outer circumferential surface of the tube body 13. The helical fin 15 extends helically around the longitudinal axis C, or the central axis of the helical unit 10.

The insertion device 2 includes a motor casing 21 attached to the manipulator 5. The motor casing 21 houses therein an electric motor 22 used as a drive source. Electric wires (not depicted) have ends connected to the electric motor 22. The electric wires extend through the manipulator 5 and the universal cord 6 and are connected to the drive control device (not depicted) as one of the peripheral devices. The drive control device controls the state in which drive electric power is supplied to the electric motor 22, thereby controlling the state in which the electric motor 22 is energized, based on an operation input that has entered into the operation input device (not depicted). When drive electric power is supplied to the electric motor 22, the electric motor 22 is energized to generate drive power for rotating, or revolving, the helical unit 10, or the driven portion 11, around the longitudinal axis C, or the central axis of the helical unit 10.

The insertion portion 3 includes a distal-end-side flexible tube portion 23 and a proximal-end-side flexible tube portion 25. The proximal-end-side flexible tube portion is disposed closer to the proximal end side than the distal-end-side flexible tube portion 23. The proximal end of the proximal-end-side flexible tube portion 25 is coupled to the manipulator 5. A base portion 27, or stator, that is made of a hard material is disposed between the distal-end-side flexible tube portion 23 and the proximal-end-side flexible tube portion 25. Specifically, the distal-end-side flexible tube portion 23 is coupled to the proximal-end-side flexible tube portion 25 through the base portion 27. With the helical unit 10 mounted on the insertion portion 3, the base portion 27 has an outer circumferential side thereof covered with the connector portion 12, or the proximal end side of the helical unit 10, of the helical unit 10. The helical unit 10 extends from a region over the outer circumferential side of the base portion 27 toward the distal end side. The distal-end-side flexible tube portion 23 has an outer circumferential side thereof covered with the driven portion 11. The number of members that the base portion 27, or stator, is made up of is not limited. The base portion 27 may be made up of a single member or may be made up of a plurality of members.

Figure 2:
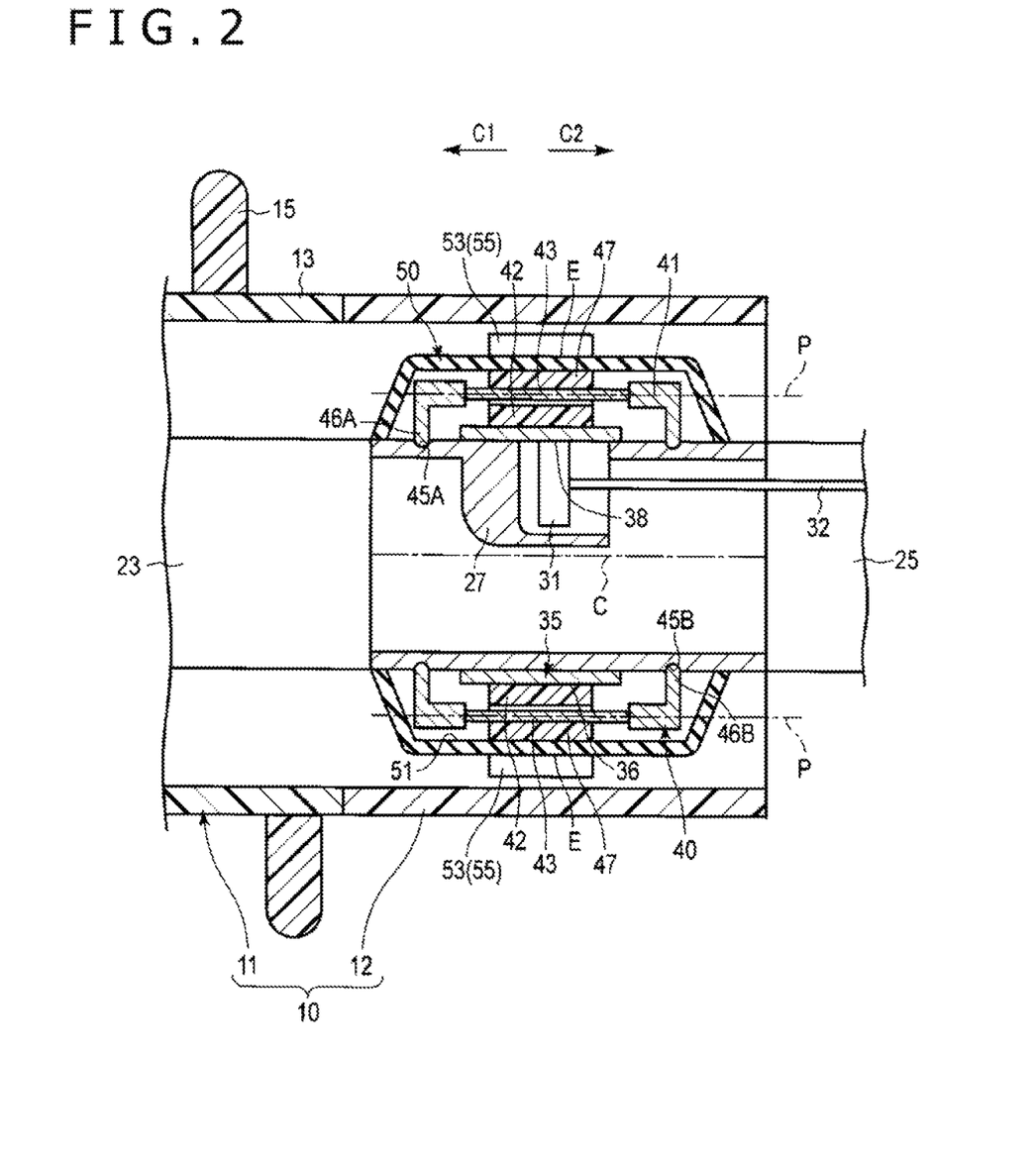
FIG. 2 is a schematic cross-sectional view, taken along a plane substantially parallel to a longitudinal axis, of a base portion and a structure in the vicinity thereof where a helical unit according to the first embodiment is mounted on an insertion portion.
Figure 3:
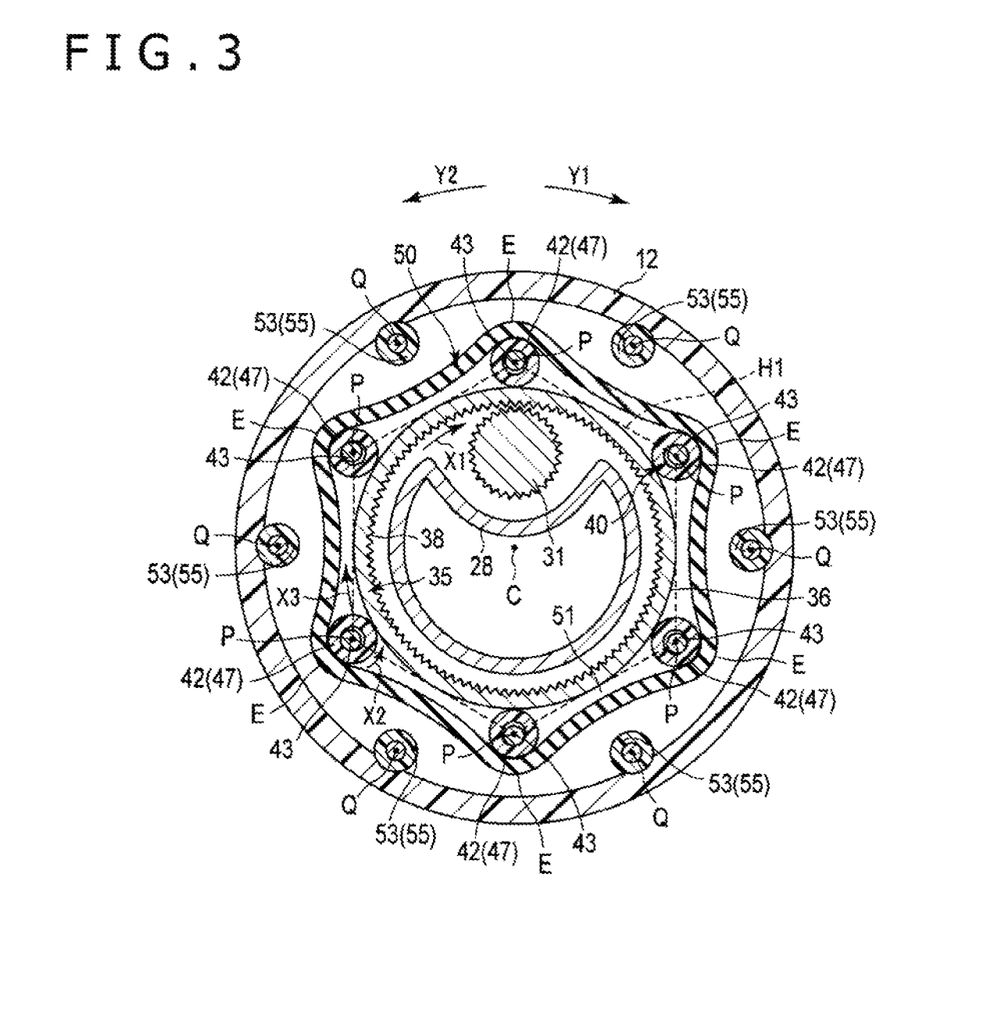
FIG. 3 is a schematic cross-sectional view, taken along a plane across the longitudinal axis through the base portion, of the base portion and the structure in the vicinity thereof where the helical unit according to the first embodiment is mounted on the insertion portion.

FIGS. 2 and 3 are views of the base portion 27 and the structure in the vicinity thereof where the helical unit 10 is mounted on the outer circumferential surface 7 of the insertion portion 3. FIG. 2 illustrates a cross section substantially parallel to the longitudinal axis C. FIG. 3 illustrates a cross section across, or substantially perpendicular to, the longitudinal axis C through the base portion 27. As depicted in FIGS. 1 through 3, a drive gear 31 is disposed in the insertion portion 3. The drive gear 31 is mounted on the base portion 27. A drive shaft 32 extends in the proximal-end-side flexible tube portion 25 from the proximal end side toward the distal end side. The drive shaft 32 has a central axis substantially parallel to the longitudinal axis C. The drive shaft 32 has a proximal end, or one end, connected to a gear train 33 in the manipulator 5. The gear train 33 is connected to the electric motor 22 used as the drive source. In other words, the drive shaft 32 is coupled to the electric motor 22 through the gear train 33. The drive shaft 32 has a distal end connected to the drive gear 31. When the electric motor 22 is energized, the drive power is transmitted therefrom through the gear train 33 to the drive shaft 32, which rotates around the central axis thereof. The drive power is thus transmitted to the drive gear 31, rotating the drive gear 31.

The insertion portion 3 includes a hollow cylindrical member 35 mounted on the outer circumferential side of the base portion 27. The hollow cylindrical member 35 is of a hollow cylindrical shape along the longitudinal axis C and has an outer circumferential surface 36. The hollow cylindrical member 35 has a central axis substantially coaxial with the longitudinal axis C. The outer circumferential surface 36 of the hollow cylindrical member 35 is of a circular shape around the longitudinal axis C in a cross section that is substantially perpendicular to the longitudinal axis C. Therefore, the outer circumferential surface 36 of the hollow cylindrical member 35 is formed as a smooth curved surface. The hollow cylindrical member 35 is rotatable around the longitudinal axis C with respect to the base portion 27. The hollow cylindrical member 35 has an internal gear 38 on an inner circumferential surface thereof. The internal gear 38 extends fully circumferentially around the longitudinal axis C. The drive gear 31 is held in mesh with the internal gear 38. When the drive gear 31 rotates, the drive power is transmitted therefrom to the hollow cylindrical member 35, which rotates, or revolves, around the longitudinal axis C. The hollow cylindrical member 35 has an outer circumferential length L1 that represents the circumferential length of the outer circumferential surface 36.

The insertion portion 3 includes a rotor 40 mounted on the base portion 27. The rotor 40 covers the outer circumferential side of the hollow cylindrical member 35. The rotor 40 is rotatable around the longitudinal axis C with respect to the base portion 27 separately from the hollow cylindrical member 35. The rotor 40 includes a tubular support member 41, or a rotary base, and a plurality of (six in the present embodiment) rollers 42, or movable members, mounted on the support member. Each of the rollers 42, or inner rollers, is supported on the support member 41 by a corresponding roller shaft 43, or a corresponding one of roller shafts 43.

The base portion 27 has engaging grooves 45A and 45B defined therein. The support member 41 has an engaging piece 46A engaging in the engaging groove 45A and an engaging piece 46B engaging in the engaging groove 45B. The rotor 40 includes the support member 41 and is mounted on the base portion 27 with the engaging pieces 46A and 46B engaging in the corresponding engaging grooves 45A and 45B. Since the rotor 40 is rotatable around the longitudinal axis C with respect to the base portion 27, the engaging pieces 46A and 46B are movable around the longitudinal axis C along the corresponding engaging grooves 45A and 45B. According to the present embodiment, the engaging groove 45A and the engaging piece 46A are positioned on a distal end side with respect to the hollow cylindrical member 35, or the internal gear 38, whereas the engaging groove 45B and the engaging piece 46B are positioned on a proximal end side with respect to the hollow cylindrical member 35, or the internal gear 38.

Each of the rollers 42, or movable members, is rotatable around a corresponding one of axes P, or can be turned around its own axis, with respect to the support member 41. In each of the rollers 42, or rotatable members, the central axis of the corresponding one of the roller shafts 43, is substantially coaxial with the corresponding one of the axes P. Accordingly, each of the own axes P extends substantially parallel to the longitudinal axis C. Each of the rollers 42 forms a corresponding one of convexities 47. Each of the convexities 47, or inner convexities, projects toward an outer circumferential side in the rotor 40. The rollers 42, or the convexities 47, are disposed at intervals spaced from each other around the longitudinal axis C.

In the cross section across, or substantially perpendicular to, the longitudinal axis C, a hexagonal shape H1, or a polygonal shape, is defined by straight lines each interconnecting a corresponding one of the axes P of the rollers 42 and the corresponding axis P of an adjacent corresponding one of the rollers 42, around the longitudinal axis C. According to the present embodiment, the rollers 42 are disposed at substantially equal intervals around the longitudinal axis C. Therefore, the hexagonal shape H1 is a regular hexagonal shape, or a regular polygonal shape, with the longitudinal axis C located at its center. Each of the respective corresponding one of the axes P, of the rollers 42 form a vertex of the hexagonal shape H1. Each of the straight lines that interconnects a corresponding one of the axes P of the rollers 42 and the corresponding axis P of an adjacent corresponding one of the rollers 42 around the longitudinal axis C forms a side of the hexagonal shape H1.

The insertion portion 3 includes a membrane 50 covering the outer circumferential side of the rotor 40 that includes the rollers 42. The membrane 50 extends along the longitudinal axis C, or the central axis of the membrane 50. The membrane 50 is made of an elastic material such as rubber, for example, and is flexible. The membrane 50 forms a part of the outer circumferential surface 7 of the insertion portion 3. The membrane 50 has a distal end and a proximal end each attached by adhesive bonding or the like to the outer circumferential surface of the base portion 27, or stator. Therefore, the membrane 50 is prevented from rotating around the longitudinal axis C, or the central axis of the membrane 50, with respect the base portion 27. Consequently, each of the hollow cylindrical member 35 and the rotor 40 is rotatable around the longitudinal axis C with respect to the membrane 50. The membrane 50 has an inner circumferential surface 51. The membrane 50 also has an inner circumferential length L2 that represents the circumferential length of the inner circumferential surface 51. The inner circumferential length L2 of the membrane 50 is larger than the outer circumferential length L1 of the hollow cylindrical member 35. The distal end of the membrane 50 is positioned on a distal end side with respect to the engaging groove 45A and the engaging piece 46A, whereas the proximal end of the membrane 50 is positioned on a proximal end side with respect to the engaging groove 45B and the engaging piece 46B.

Each of the rollers 42, or the convexities 47, presses the membrane 50 from the inner circumferential side thereof toward the outer circumferential side thereof. Therefore, the membrane 50 is elastically deformed by being pressed by the rollers 42, or movable members, and protrudes toward the outer circumferential side at the position, or location, where the membrane 50 is pressed by each of the rollers 42. The membrane 50 thus forms on its outer circumferential surface a corresponding one of vertexes E protruding toward the outer circumferential side at the position where the membrane 50 is pressed by each of the rollers 42 around the longitudinal axis C. The membrane 50 as it is elastically deformed exerts an elastic force to each of the rollers 42 toward the inner circumferential side of the rotor 40. In other words, the membrane 50 urges each of the rollers 42 toward the longitudinal axis C. Therefore, the membrane 50 is pressed against each of the rollers 42 from the outer circumferential side thereof.

Each of the rollers 42 has a hole defined therein through which the corresponding one of the roller shafts 43 is inserted. The hole has a diameter slightly larger than the diameter of the corresponding one of the roller shafts 43. Consequently, each of the rollers 42, or movable members, is supported on the support member 41 so as to be displaceable in radial directions around the longitudinal axis C. According to an embodiment, each of the roller shafts 43 corresponding to the respective rollers 42 is made of an elastic material. In this case, each of the rollers 42, or movable members, is also supported on the support member 41 so as to be displaceable in radial directions around the longitudinal axis C.

In the rotor 40, each of the rollers 42, or movable members, is held against the outer circumferential surface 36 of the hollow cylindrical member 35 from the outer circumferential side. As described hereinbefore, each of the rollers 42 is urged toward the longitudinal axis C by the membrane 50 and is displaceable in the radial directions around the longitudinal axis C. Consequently, each of the rollers 42 is pressed against the outer circumferential surface 36 of the hollow cylindrical member 35 by being urged by the membrane 50. The rollers 42 are thus held against the outer circumferential surface 36 of the hollow cylindrical member 35 from the outer circumferential side. Since each of the rollers 42 is pressed toward the longitudinal axis C by the membrane 50, a clearance is defined between the inner circumferential side of each of the roller shafts 43 and the corresponding one of the rollers 42 in the radial directions around the longitudinal axis C.

When the hollow cylindrical member 35 is rotated around the longitudinal axis C by the transmitted drive power, the drive power is transmitted to each of the rollers 42, or movable members, that is held against the inner circumferential surface 51 of the membrane 50 and the outer circumferential surface 36 of the hollow cylindrical member 35. Each of the rollers 42 is thus rotated, or turned around its own axis, around the corresponding one of the axes P with respect to the support member 41. At this time, each of the rollers 42 is turned around its own axis in a direction opposite to the direction of rotation of the hollow cylindrical member 35. For example, when the hollow cylindrical member 35 is rotated in one direction (as indicated by the arrow Y1) around the longitudinal axis C, i.e., clockwise in FIG. 3 (as indicated by the arrow X1 in FIG. 3), each of the rollers 42 is rotated counterclockwise in FIG. 3 (as indicated by the arrow X2 in FIG. 3) around the corresponding one of the axes P.

When the drive power is transmitted to each of the rollers 42, or movable members, that is held against the inner circumferential surface 51 of the membrane 50 and the outer circumferential surface 36 of the hollow cylindrical member 35 by the rotation of the hollow cylindrical member 35 around the longitudinal axis C, each of the rollers 42 is moved, or revolved, around the longitudinal axis C with respect to the membrane 50. The movement of each of the rollers 42 around the longitudinal axis C causes the rotor 40 that includes the support member 41 and the rollers 42 to rotate in unison around the longitudinal axis C with respect to the base portion 27 and the membrane 50. At this time, the side toward which the rotor 40 is rotated around the longitudinal axis C, or the side to which each of the rollers 42 is moved around the longitudinal axis C, is the same as the side toward which the hollow cylindrical member 35 is rotated around the longitudinal axis C. For example, when the hollow cylindrical member 35 is rotated in one direction (as indicated by the arrow Y1) around the longitudinal axis C, i.e., clockwise in FIG. 3 (as indicated by the arrow X1 in FIG. 3), each of the rollers 42 is rotated clockwise in FIG. 3 (as indicated by the arrow X3 in FIG. 3) around the longitudinal axis C.

A plurality of (six in the present embodiment) rollers 53 are mounted on the inner circumferential surface of the connector portion 12 of the helical unit 10, or mount tool. Each of the rollers 53, or outer rollers, can be turned around a corresponding one of axes Q. Each of the own axes Q extends substantially parallel to the longitudinal axis C. According to the present embodiment, each of the rollers 53 forms a corresponding one of convexities 55. Each of the convexities 55, or outer convexities, protrudes from an inner circumferential surface of the connector portion 12 toward an inner circumferential side. The convexities 55, or the rollers 53, are disposed at intervals spaced from each other around the longitudinal axis C. With the helical unit 10 mounted on the insertion portion 3, i.e., with the connector portion 12 covering the outer circumferential side of the membrane 50, each of the convexities 55, or outer convexities, is disposed between adjacent corresponding two of the convexities 47 around the longitudinal axis C.

When the rotor 40 that includes the rollers 42 is rotated about the longitudinal axis C as described hereinbefore, each of the convexities 47, or inner convexities, i.e., each of the vertexes E formed on the membrane 50, moves around the longitudinal axis C. Upon the movement of the convexities 47 around the longitudinal axis C with the helical unit 10 mounted on the insertion portion 3, each of the convexities 47, or inner convexities, presses a corresponding one of the convexities 55 through the membrane 50. As each of the convexities 55, or outer convexities, is pressed, the drive power is transmitted to the helical unit 10. The helical unit 10 includes the driven portion 11 and the connector portion 12. The helical unit 10 is rotated around the longitudinal axis C with respect to the base portion 27 and the membrane 50. At this time, the side toward which the helical unit 10 is rotated around the longitudinal axis C is the same as the side toward which the rotor 40 is rotated around the longitudinal axis C, or the side toward which each of the rollers 42 is moved around the longitudinal axis C.

Next, operation and advantages of the endoscope 1 according to the present embodiment will be described. For observing a lumen using the endoscope 1, the helical unit 10, or mount tool, is mounted on the insertion portion 3 of the insertion device 2, or insertion tool. The insertion portion 3 and the helical unit 10 are inserted into the lumen. The user enters an "operation input" into the operation input device (not depicted), energizing the electric motor 22, or drive source. The drive power is transmitted from the motor 22 through the insertion portion 3 to the helical unit 10 as described hereinbefore. The helical unit 10 is now rotated around the longitudinal axis C. Because the helical unit 10 is rotated while the helical fin 15 is being pressed toward the inner circumferential side by the lumen wall, a propulsive force toward the distal end side or the proximal end side, or in one of the directions along the longitudinal axis C, acts on the insertion portion 3 and the helical unit 10. The propulsive force increases the mobility of the insertion portion 3 in the lumen. Inasmuch as each of the rollers 42 is rotatable about the corresponding one of the axes P, the friction between each of the rollers 42 and the membrane 50 is reduced. Similarly, since each of the rollers 53 is rotatable about the corresponding one of the axes Q the friction between each of the rollers 53 and the membrane 50 is reduced.

According to the present embodiment, since the drive power for rotating the helical unit 10 is transmitted as described hereinbefore, the rotational speed V2 of the rotor 40 that is rotated around the longitudinal axis C is reduced with respect to the rotational speed V1 of the hollow cylindrical member 35, or the internal gear 38. Using the outer circumferential length L1 of the hollow cylindrical member 35 and the inner circumferential length L2 of the membrane 50, the relationship between the rotational speed V1 and the rotational speed V2 is expressed by the equation (1). The rotational speed V2 represents the speed at which the rollers 42 move.

$$V2 = V1 / \left\{ \left( \frac{L2}{L1} \right) + 1 \right\} \quad (1)$$

Since the rotational speed V2 of the rollers 42 are rotated around the longitudinal axis C and is reduced with respect to the rotational speed V1 of the hollow cylindrical member 35 as described hereinbefore, the rotational torque τ2 of the rotor 40, or the rollers 42, around the longitudinal axis C is amplified with respect to the rotational torque τ1 of the hollow cylindrical member 35 around the longitudinal axis C. In other words, according to the present embodiment, the transmission efficiency with which the rotational torque, or drive torque, is transmitted from the hollow cylindrical member 35 to the rotor 40 is increased. Therefore, the rotational torque τ2 that is of an appropriate magnitude is applied to the rotor 40. Furthermore, the rotational speed V3 of the helical unit 10, or mount tool, that is rotated around the longitudinal axis C is substantially the same as the rotational speed V2 of the rotor 40 that is rotated around the longitudinal axis C. The rotational torque τ3 of the helical unit 10 around the longitudinal axis C is the same as the rotational torque τ2 of the rotor 40, or the rollers 42, around the longitudinal axis C. Consequently, as the rotational torque τ2 of the rotor 40 around the longitudinal axis C is of an appropriate magnitude, the rotational torque τ3 that is of an appropriate magnitude is applied to the helical unit 10, or mount tool.

According to the present embodiment, moreover, since the rotational torque τ2, or drive torque, of the rotor 40, or the rollers 42, around the longitudinal axis C is amplified with respect to the rotational torque τ1, or drive torque, of the hollow cylindrical member 35, it is not necessary to increase the rotational torque τ1 applied to the internal gear 38, or the hollow cylindrical member 35. Therefore, it is possible to make the rotational speed V1 of the internal gear 38, or the hollow cylindrical member 35 large, compared with the background art. It is possible to reduce the rotational torque τ1 of the hollow cylindrical member 35 around the longitudinal axis C. In other words, even though the rotational torque τ1 of the hollow cylindrical member 35 is small, it is possible to increase the rotational torque τ2 of the rotor 40 and to increase the rotational torque τ3 of the helical unit 10. Therefore, it is possible to reduce the extent to which the torque is amplified, or the extent to which the speed is reduced, in the structure that transmits the drive power from the electric motor 22, or drive source, to the hollow cylindrical member 35, or the internal gear 38. The structure that transmits the drive power from the electric motor 22 to the hollow cylindrical member 35 can thus be simplified and reduced in size. As the structure that transmits the drive power in the insertion portion 3 is simplified and reduced in size, the expenditure of labor and cost in the manufacture of the insertion portion 3 is reduced.

When the endoscope 1 is in use, if a load for stopping the driven portion 11 from rotating becomes excessively large, e.g., if a pressing force applied from the lumen wall or the like to the driven portion 11 becomes excessively large, then a load on the rotor 40 also becomes excessively large. According to the present embodiment, the rollers 42 of the rotor 40 are held in contact with the outer circumferential surface 36 of the hollow cylindrical member 35 which is a smooth curved surface, or a hollow cylindrical curved surface. Therefore, if a load for stopping the helical unit 10 from rotating becomes excessively large, the outer rollers 53 prevent the inner rollers 42 from revolving around the longitudinal axis C. When the inner rollers 42 are prevented from revolving around the longitudinal axis C, the rotator 40 is also prevented from revolving around the longitudinal axis C. At this time, each of the rollers 42 slips against the outer circumferential surface 36 of the hollow cylindrical member 35. Consequently, even when the hollow cylindrical member 35 is rotated about the longitudinal axis C by the drive power transmitted from the electric motor 22, the drive power is not transmitted from the hollow cylindrical member 35 to each of the rollers 42. Even when the hollow cylindrical member 35 is rotated about the longitudinal axis C, the rotor 40 that includes the rollers 42 is not rotated (revolved) around the longitudinal axis C. Therefore, while an excessive load is being imposed on the helical unit 10 and the rotor 40, the drive power is prevented from being transmitted to the helical unit 10 and the rotor 40. Also, the helical unit 10 is prevented from rotating around the longitudinal axis C. In other words, the rollers 42 and the hollow cylindrical member 35 form a mechanical torque limit.

At this time, each of the rollers 42 is displaceable in the radial directions around the longitudinal axis C due to the clearance between the roller 42 and the corresponding roller shaft 43, or the corresponding one of the roller shafts 43. Therefore, each of the rollers 42 is slightly displaced, or produces backlash, toward the outer circumferential side, or the inner circumferential surface of the membrane 50, in the radial directions around the longitudinal axis C. The frictional force between (i) the outer circumferential surface of the hollow cylindrical member 35 that are rotated around the longitudinal axis C and (ii) the outer circumferential surfaces of the rollers 42 that are not revolved around the longitudinal axis C is thus reduced. Therefore, the load imposed on the electric motor 22 as the drive source for rotating the hollow cylindrical member 35 is reduced in a manner to be commensurate with the reduction in the frictional force between the hollow cylindrical member 35 and the rollers 42.

According to the present embodiment, furthermore, the hollow cylindrical member 35 has the internal gear 38 on the inner circumferential surface thereof, and the rollers 42 are included in the rotor 40 that is separate from the hollow cylindrical member 35. Consequently, the hollow cylindrical member 35 and the rotor 40 can be machined to shape more easily than if an internal gear (38) is formed and rollers (42) are mounted on one member as is the case with the background art. The expenditure of labor and cost in the manufacture of the insertion portion 3 is thus further reduced.

The number of the rollers 42, or movable members, of the rotor 40 is not limited to the number in the embodiment described hereinbefore, etc. The number of the rollers 42, or the convexities 47, may be more than one, and is not limited to six.

The number of the convexities 55, or the rollers 53, of the helical unit 10 is not limited to the number in the embodiment described hereinbefore, etc. The number of the convexities 55, or the rollers 53, may be more than one, and is not limited to six.

In the embodiment described hereinbefore, etc., each of the rollers 53 in the helical unit 10 forms a corresponding one of the convexities 55, or outer convexities. However, such an arrangement is not restrictive. According to a modification, a helical unit (10) is free of rollers (53) and all convexities (55) are integrally formed of a single member on a connector portion (12). In this modification, when a rotor (40) is rotated around the longitudinal axis C, each of convexities (47) of the rotor (40) presses a corresponding convexity (55), or a corresponding one of convexities (55), through a membrane (50). The drive power is thus transmitted to the helical unit (10), rotating the helical unit (10) about the longitudinal axis C.

According to a modification not illustrated, a helical unit (10) may be free of convexities (55). In this case, a hollow cylindrical ring member whose inner circumferential surface is formed as a smooth curved surface is disposed on a connector portion (12) of the helical unit (10). The ring member is made of an elastic material and is flexible. With the helical unit (10) mounted on an insertion portion (3), the ring member presses each of convexities (47), the rollers (42), of a rotor (40) toward an inner circumferential side through a membrane (50). The ring member has an inner circumferential surface held against an outer circumferential side of each of vertexes (E) of the membrane (50) that are formed by the convexities (47).

According to the present modification, as with the first embodiment, when a hollow cylindrical member (35) of the insertion portion (3) is rotated about a longitudinal axis (C), the drive power is transmitted to the rotor (40). Each of the rollers (42) is rotated about its own axis (P), or a corresponding one of the axes (P), and moved, or revolved, around the longitudinal axis (C). As each of the rollers (42), or the convexities (47), is moved around the longitudinal axis (C), a progressive wave is developed in the membrane (50) and travels toward the side to which the convexities (47) move around the longitudinal axis (C).

As the progressive wave moves, each spot on the outer circumferential surface of the membrane (50) makes an elliptical motion. The rotation of the elliptical motion is opposite to the movement of the convexities (47). Due to the elliptical motion of the outer circumferential surface of the membrane (50), at a position where each of the convexities (47) presses the membrane (50) toward the outer circumferential side, or at each of vertexes (E) of the membrane (50) that protrudes toward the outer circumferential side, a force, or frictional force, acts on the ring member held against the convexities from the outer circumferential side toward a side opposite to the side to which the progressive wave moves. The helical unit (10) including the ring member is rotated by the force around the longitudinal axis (C) toward the side opposite to the side to which the progressive wave moves. According to the present modification, therefore, the helical unit (10) including the ring member is rotated toward the side opposite to the side to which the rotor (40) is rotated around the longitudinal axis (C).

According to the embodiment described hereinbefore, etc., the helical unit (10) has been illustrated as an example of the mount tool mounted on the insertion portion (3). However, the mount tool is not limited to the helical unit (10). For example, a mount tool according to a modification includes a belt member held against a driven portion (11) from the outer circumferential side thereof. In this case, when the driven portion (11) is rotated around the longitudinal axis (C), the drive power is transmitted from the driven portion (11) to the belt member, moving the belt member toward a proximal end side or a distal end side. According to the present modification, therefore, when the drive power is transmitted, a portion of the mount tool is rotated around the longitudinal axis (C).

According to the embodiment described hereinbefore, etc., the insertion device (2) has been illustrated. However, the arrangement described hereinbefore may be applied to an insertion apparatus in which a manipulator is used as an insertion device, for example.

According to the embodiment described hereinbefore, etc., the insertion device (2) includes the insertion portion (3) extending along the longitudinal axis (C), and the insertion portion (3) includes the hollow cylindrical member (35) formed in a hollow cylindrical shape along the longitudinal axis (C) and rotatable about the longitudinal axis (C) by the drive power transmitted thereto. The insertion portion (3) includes at least one movable member (42) held in contact with the outer circumferential surface (36) of the hollow cylindrical member (35). The movable member (42) is rotatable about its own axis (P) parallel to the longitudinal axis (C) and movable around the longitudinal axis (C) when the drive power is transmitted thereto from the hollow cylindrical member (35) as the hollow cylindrical member (35) is rotated around the longitudinal axis (C). In the insertion portion (3), the membrane (50) forms a part of the outer circumferential surface (7) in covering relation to the movable member (42) from the outer circumferential side thereof. The membrane (50) is flexible, and urges the movable member (42) toward the longitudinal axis (C), pressing the movable member (42) against the outer circumferential surface (36) of the hollow cylindrical member (35).

The present disclosure is not limited to the above embodiment, but various changes and modifications may be made therein without departing from the scope of the invention when the invention is reduced to practice. The embodiment may be carried out in appropriate combinations, obtaining combined advantages. The above embodiment covers inventions at various stages such that various inventions can be extracted by appropriate combinations of a plurality of components that are disclosed.

In sum, the disclosed technology is directed to an insertion device used in an endoscope system comprises an insertion portion extending along a longitudinal axis. The insertion portion having a hollow cylindrical member having a central axis corresponding to the longitudinal axis and having an outer circumferential surface and rotatable about the longitudinal axis by a drive power transmitted to the hollow cylindrical member. At least one movable member is held in contact with the outer circumferential surface. The movable member rotates about an axis thereof parallel to the longitudinal axis and movable around the longitudinal axis when the drive power is transmitted to the movable member from the hollow cylindrical member while the hollow cylindrical member is rotated around the longitudinal axis. A membrane forms a part of an outer circumferential surface of the insertion portion in covering relationship with respect to the movable member from an outer circumferential side thereof. The membrane is flexible and urges the movable member toward the longitudinal axis and presses the movable member against the outer circumferential surface of the hollow cylindrical member.

The movable member is supported so as to be displaceable in radial directions around the longitudinal axis. The insertion device further comprises a tubular support member supporting the movable member thereon and rotates about the longitudinal axis in unison with the movable member when the movable member is rotated around the axis thereof and is moved around the longitudinal axis. The movable member is movable around the longitudinal axis at a first speed reduced with respect to a second speed at which the hollow cylindrical member is rotated around the longitudinal axis. The at least one movable member includes a plurality of movable members disposed at intervals spaced from each other around the longitudinal axis. The insertion device in which in a cross section along the longitudinal axis, a polygonal shape is defined by straight lines each interconnecting the own axis of each of the movable members and the own axis of an adjacent one of the movable members around the longitudinal axis.

An endoscope comprises a mount tool and an insertion portion extending along a longitudinal axis. The insertion portion includes a hollow cylindrical member having a central axis corresponding to the longitudinal axis having an outer circumferential surface and being rotatable about the longitudinal axis by a drive power being transmitted to the hollow cylindrical member. At least one movable member is held in contact with the outer circumferential surface. The movable member is rotatable about an axis thereof parallel to the longitudinal axis and being movable around the longitudinal axis when the drive power is transmitted to the movable member from the hollow cylindrical member while the hollow cylindrical member is being rotated around the longitudinal axis. A membrane forms a part of an outer circumferential surface of the insertion portion in covering relation to the movable member from an outer circumferential side thereof. The membrane is flexible and urges the movable member toward the longitudinal axis and presses the movable member against the outer circumferential surface of the hollow cylindrical member. The mount tool is mounted on the insertion portion in covering relationship with respect to the outer circumferential side of the membrane. The drive power is transmitted to the mount tool from the movable member when the movable member is moved around the longitudinal axis.

The movable member is supported so as to be displaceable in radial directions around the longitudinal axis. The endoscope further comprises a tubular support member supporting the movable member thereon and rotates about the longitudinal axis in unison with the movable member when the movable member is rotated around an axis thereof and is moved around the longitudinal axis. The movable member is movable around the longitudinal axis at a first speed reduced with respect to a second speed at which the hollow cylindrical member is rotated around the longitudinal axis. The at least one movable member includes a plurality of movable members disposed at intervals spaced from each other around the longitudinal axis. The plurality of movable members are defined by six movable members. The endoscope in which in a cross section along the longitudinal axis, a polygonal shape is defined by straight lines each interconnecting the own axis of each of the movable members and the own axis of an adjacent one of the movable members around the longitudinal axis.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An insertion device used in an endoscope system comprising:
   an insertion portion extending along a longitudinal axis;
   the insertion portion including:
      a hollow cylindrical member having a central axis corresponding to the longitudinal axis, having an outer circumferential surface and rotatable about the longitudinal axis by a drive power transmitted to the hollow cylindrical member;
      at least one roller being held in contact with the outer circumferential surface, the at least one roller being rotatable about an axis thereof parallel to the longitudinal axis and movable around the longitudinal axis when the drive power is transmitted to the at least one roller from the hollow cylindrical member while the hollow cylindrical member is rotated around the longitudinal axis; and
      a membrane forming a part of an outer circumferential surface of the insertion portion in covering relationship with respect to the at least one roller from an outer circumferential side thereof, the membrane being flexible and urges the at least one roller toward the longitudinal axis and presses the at least one roller against the outer circumferential surface of the hollow cylindrical member,
wherein the at least one roller is supported so as to be displaceable in radial directions around the longitudinal axis.

2. The insertion device of claim 1 further comprising:
a tubular support member supporting the at least one roller thereon and rotatable about the longitudinal axis in unison with the at least one roller when the at least one roller is rotated around the axis thereof and is moved around the longitudinal axis.

3. The insertion device of claim 1, wherein the at least one roller is movable around the longitudinal axis at a first speed reduced with respect to a second speed at which the hollow cylindrical member is rotated around the longitudinal axis.

4. The insertion device of claim 1, wherein the at least one roller includes a plurality of rollers disposed at intervals spaced from each other around the longitudinal axis.

5. The insertion device of claim 4, wherein in a cross section along the longitudinal axis, a polygonal shape is defined by straight lines each interconnecting the own axis of each of the plurality of rollers and the own axis of an adjacent one of the plurality of rollers around the longitudinal axis.

6. An endoscope comprising:
a mount tool; and
an insertion portion extending along a longitudinal axis, wherein the insertion portion includes:
a hollow cylindrical member having a central axis corresponding to the longitudinal axis having an outer circumferential surface and being rotatable about the longitudinal axis by a drive power being transmitted to the hollow cylindrical member;
at least roller being held in contact with the outer circumferential surface, the at least one roller being rotatable about an axis thereof parallel to the longitudinal axis and being movable around the longitudinal axis when the drive power is transmitted to the at least one roller from the hollow cylindrical member while the hollow cylindrical member is being rotated around the longitudinal axis; and
a membrane forming a part of an outer circumferential surface of the insertion portion in covering relation to the at least one roller from an outer circumferential side thereof, the membrane being flexible and urges the at least one roller toward the longitudinal axis and presses the at least one roller against the outer circumferential surface of the hollow cylindrical member, wherein
the mount tool is mounted on the insertion portion in covering relationship with respect to the outer circumferential side of the membrane, wherein the drive power being transmitted to the mount tool from the at least one roller when the at least one roller is moved around the longitudinal axis, and
the at least one roller is supported so as to be displaceable in radial directions around the longitudinal axis.

7. The endoscope of claim 6 further comprising:
a tubular support member supporting the at least one roller thereon and rotatable about the longitudinal axis in unison with the at least one roller when the at least one roller is rotated around an axis thereof and is moved around the longitudinal axis.

8. The endoscope of claim 6, wherein the at least one roller is movable around the longitudinal axis at a first speed reduced with respect to a second speed at which the hollow cylindrical member is rotated around the longitudinal axis.

9. The endoscope of claim 6, wherein the at least one roller includes a plurality of rollers disposed at intervals spaced from each other around the longitudinal axis.

10. The endoscope of claim 9, wherein in a cross section along the longitudinal axis, a polygonal shape is defined by straight lines each interconnecting the own axis of each of the plurality of rollers and the own axis of an adjacent one of the plurality of rollers around the longitudinal axis.

11. The endoscope of claim 6, wherein the plurality of rollers are defined by six rollers.

* * * * *